United States Patent [19]

Prencipe et al.

[11] Patent Number: 5,730,959
[45] Date of Patent: *Mar. 24, 1998

[54] STORAGE STABLE AQUEOUS DENTIFRICE COMPOSITIONS HAVING IMPROVED ANTICALCULUS PROPERTIES

[75] Inventors: Michael Prencipe, West Windsor; Michael A. Collins, Hazlet, both of N.J.

[73] Assignee: Colgate Palmolive Company, New York, N.Y.

[*] Notice: The term of this patent shall not extend beyond the expiration date of Pat. No. 5,599,527.

[21] Appl. No.: 790,348

[22] Filed: Jan. 24, 1997

Related U.S. Application Data

[63] Continuation-in-part of Ser. No. 340,568, Nov. 14, 1994, Pat. No. 5,599,527.

[51] Int. Cl.$^6$ ............... A61K 7/16; A61K 7/18; A61K 7/20
[52] U.S. Cl. ............... 424/52; 424/49; 424/53; 424/57
[58] Field of Search ............... 424/49, 52, 53, 424/57

[56] References Cited

U.S. PATENT DOCUMENTS

| | | | |
|---|---|---|---|
| 2,511,249 | 6/1950 | Durgin et al. | 23/106 |
| 4,627,977 | 12/1986 | Gaffar et al. | 424/52 |
| 4,777,026 | 10/1988 | Griffith | 423/305 |
| 4,798,712 | 1/1989 | Peterson | 423/315 |
| 4,808,400 | 2/1989 | Gaffar et al. | 424/52 |
| 4,889,712 | 12/1989 | Gaffar et al. | 424/52 |
| 4,894,220 | 1/1990 | Nabi et al. | 424/52 |
| 4,913,895 | 4/1990 | Miyake et al. | 424/57 |
| 4,915,937 | 4/1990 | Amjad | 424/52 |
| 5,302,363 | 4/1994 | Highfill et al. | 423/315 |
| 5,599,527 | 2/1997 | Hsu et al. | 424/52 |

*Primary Examiner*—Shep K. Rose
*Attorney, Agent, or Firm*—Paul Shapiro

[57] ABSTRACT

A storage stable aqueous oral composition which is effective against calculus which contains an orally acceptable vehicle having incorporated therein from about 10% to up to about 15% by weight water, an effective anticalculus combination of about 0.5 to about 2% by weight of a water soluble pyrophosphate salt and about 0.5 to about 3% by weight of a water soluble polyphosphate salt. The presence in the composition of relatively high amounts of water affect the stability of the composition.

20 Claims, No Drawings

STORAGE STABLE AQUEOUS DENTIFRICE COMPOSITIONS HAVING IMPROVED ANTICALCULUS PROPERTIES

This application is a continuation-in-part of patent application U.S. Ser. No. 08/340,568 filed Nov. 14, 1994, now U.S. Pat. No. 5,599,527.

BACKGROUND OF THE INVENTION

1. Field of the Invention

The invention relates generally to a dentifrice composition and more particularly to an aqueous, storage dentifrice composition which contains reactive ingredients and exhibits improved anticalculus properties.

2. The Prior Art

It has been found to be very desirable to incorporate peroxide compounds in dentifrice compositions, the efficacy of peroxide compounds in oral hygiene having long been recognized. Such compounds have been proven effective in the treatment of gingivitis, periodontitis and in combating plaque. Additionally, peroxide compounds have been utilized for oral cosmetic purposes such as tooth whitening which results from bleaching and cleansing of tooth surfaces. Examples of the prior art disclosing peroxide containing dentifrices are found in the disclosures of U.S. Pat. No. 4,971,782, U.S. Pat. No. 4,897,258 and U.S. Pat. No. 4,837,008.

Although the presence of peroxide ingredients in the dentifrice provides antiplaque and whitening efficacy, an improvement in the anticalculus (i.e., antitartar) efficacy of the dentifrice is desired by the art.

Included in the wide variety of chemical agents disclosed by the prior art as being effective as anticalculus agents are the water soluble polyphosphate and pyrophosphate salts. For example, U.S. Pat. No. 4,923,684 and U.S. Pat. No. 4,985,236 disclose the use of a water-soluble alkali metal tripolyphosphate as an anticalculus agent in dentifrice compositions. The patent discloses that to be storage stable, the tripolyphosphate salt must be incorporated in the dentifrice at a concentration of at least 4% by weight, the dentifrice having an alkaline pH, for example, a pH of 8–10. At concentrations less than 4% by weight, for example, 3% by weight, the patent teaches that the polyphosphate salt is unstable in the stored dentifrice composition.

U.S. Pat. No. 4,684,518 discloses that water soluble alkali metal pyrophosphate salts are effective as anticalculus agents when present in dentifrice compositions at a concentration sufficient to provide at least 1.5% $P_2O_7^{-4}$ anion.

U.S. Pat. No. 5,176,900 discloses a dentifrice composition containing an anticalculus combination of a water soluble tripolyphosphate salt sufficient to provide 0.5–7.5% $P_3O_{10}$ anion and a water soluble orthophosphate salt sufficient to provide from 0.2–5% orthophosphate anion, the combination being storage stable at a pH below 8.0.

SUMMARY OF THE INVENTION

In patent application U.S. Ser. No. 08/340,568, now U.S. Pat. No. 5,599,527 referred to above there is disclosed a storage stable oral composition which is effective against calculus which contains an orally acceptable vehicle having incorporated therein an effective anticalculus combination of about 0.5 to about 2% by weight of a water soluble pyrophosphate salt and about 0.5 to about 3% by weight of a water soluble polyphosphate salt. The oral composition exhibits an anticalculus efficacy at least equivalent to that exhibited by presently available commercial dentifrice products delivering an anticalculus benefit.

U.S. Ser. No. 08/340,568, Now U.S. Pat. No. 599,527 also discloses that when the amount of water present in the dentifrice composition is maintained at a concentration of less than about 9%, by weight the free pyrophosphate ion concentration incorporated in the dentifrice is maintained at substantially the original levels of incorporation in the dentifrice during storage, in spite of the presence in the dentifrice of reactive ingredients such as peroxide and bicarbonate compounds as well as polyvalent metal cations, such as calcium ion, which is normally incompatible with water soluble fluoride and pyrophosphate salts as these polyvalent cations normally interact to form water insoluble salts which are inactive in the aqueous environment of the oral cavity.

According to the disclosure of U.S. Ser. No. 08/340,568 concentrations of water in the dentifrice composition above about 9% by weight were believed to adversely effect the stability of such compositions. It has now been expectedly determined that, contrary to the teachings of U.S. Ser. No. 08/340,568, now U.S. Pat. No. 5,599,527 concentrations of water of 10% by weight do not adversely effect stability, and that water in amounts up to about 15% by weight can be tolerated in the oral composition.

In accordance with the present invention there is provided an aqueous fluoride gel or paste which is storage stable and is effective against calculus, comprising a vehicle containing in excess of about 9% by weight water and up to about 15% by weight water having incorporated therein a water soluble fluoride compound providing about 10 to 2,000 ppm fluoride ion and a combination of about 0.5 to no more than about 3% by weight of a water soluble alkali metal polyphosphate and about 0.5 to no more than about 2.0% by weight of a water soluble alkali metal pyrophosphate which composition is stable and effective to reduce calculus formation on teeth in the oral cavity.

DESCRIPTION OF THE PREFERRED EMBODIMENTS

The vehicle used to prepare the oral gel or paste composition of the present invention may be substantially anhydrous or contain limited amounts of water as well as a suitable humectant such as glycerin, sorbitol, polyethylene glycol, or any suitable mixture thereof. Water is included in the vehicle of the composition preferably at a concentration of no more than about 15% by weight of the composition and most preferably about 10 to about 15% by weight without adversely affecting the stability of the composition.

The proportion of vehicle used to prepare the oral composition of the present invention is generally within the range of about 40 to about 70% by weight of the composition of this invention and preferably about 50 to about 65% by weight of the composition. Glycerin is present in the vehicle of the present invention at a concentration of about 10 to about 60% by weight of the composition and preferably about 15 to about 40% by weight of the composition.

A surfactant is used in the preparation of composition of the present invention to aid in the thorough dispersion of the dentifrice composition throughout the oral cavity when applied thereto as well as to improve the cosmetic acceptability and detersive and foaming properties of the composition. Among the organic surfactants useful in the practice of the present invention are salts of the higher alkyl sulfates, such as sodium lauryl sulfate (SLS) or other suitable alkyl sulfate having 8 to 18 carbon atoms in the alkyl group;

sodium lauryl sulfoacetate, salts of sulfonated monoglycerides of higher fatty acids, such as sodium coconut monoglyceride sulfonate or other suitable sulfonated monoglycerides of a fatty acids of 10 to 18 carbon atoms; salts of amides of higher fatty acid, e.g., 12 to 16 carbon atom acids, with lower aliphatic amino acids, such as sodium-N-methyl-N-palmitoyl tauride, sodium N-lauroyl-, N-myristoyl- and N-palmitoyl sarcosinates; salts of the esters of such fatty acids with isothionic acid or with glycerol monosulfate, such as the sodium salt of monosulfated monoglyceride of hydrogenated coconut oil fatty acids; salts of olefin sulfonates, e.g. alkene sulfonates or hydroxalkene sulfonates or mixtures thereof having 12 to 16 carbon atoms in the carbon chain of the molecule; and soaps of higher fatty acids, such as those of 12 to 18 carbon atoms, e.g., coconut fatty acids. The cation of the salt may be sodium potassium or mono-, di or triethanol amine.

The surfactant is included in the vehicle of the present invention at a concentration of about 0.5 to about 3.0% by weight of the composition and preferably about 1.0 to about 2.0% by weight of the composition.

Polishing agents are incorporated in dentifrice composition of the present invention and preferred polishing agents are siliceous materials, such as silica, and will normally have a mean particle size up to about 10 microns and a very high surface area, e.g. in the range of 150–750 square meters/gram. A preferred silica is a precipitated amorphous hydrated silica, such as Sorbosil AC-35 marketed by Crosfield Chemicals, or Zeodent 115 from J. M. Huber Company but other polishing agents may also be employed, including sodium bicarbonate, calcium carbonate, sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, alumina trihydrate, aluminum silicate, zirconium silicate, calcined alumina and bentonite.

The polishing agent is present in the composition of the present invention at a concentration of about 10 to about 30% by weight and preferably about 5 to about 25% by weight.

Bicarbonate compounds, when included the composition of the present invention, are included at a concentration of about 5 to about 20% by weight and preferably about 8 to about 15% by weight. When used at these concentrations the pH of the composition is generally in the range of about 8 to about 10. The particle size of the bicarbonate compound can range from about 10 to about 300 microns although a particle size of 20–60 microns is preferred, the smaller particle size bicarbonate being more readily dispersed in the anhydrous vehicle.

Inorganic thickeners may be included in the composition of the present invention and include fumed silicas such as Cab-o-sil available from Cabot Corporation, and thickening silicas including those available from W. R. Grace designated Sylox 15.

Organic thickeners such as natural and synthetic gums and colloids may also be incorporated in the gel or paste composition of the present invention. Examples of such thickeners include carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose.

The inorganic or organic thickener may be incorporated in the compositions of the present invention at a concentration of about 0.05 to about 2% by weight and preferably about 0.1 to about 1.5% by weight.

Peroxide compounds may be used as an ingredient in the composition of the present invention and when added to the composition are present at a concentration of about 0.25 to about 5% by weight and preferably about 0.5 to about 2.0% by weight. Peroxide compounds suitable for use in the practice of the present invention include metal peroxides such as calcium peroxide, magnesium peroxide and zinc peroxide.

Fluoride-providing salts having anti-caries efficacy may also be incorporated in the dentifrice of the present invention and are characterized by their ability to release fluoride ions in water. It is preferable to employ a water-soluble salt fluoride providing about 10–2,000 ppm of fluoride ion, and preferably about 1000–1500 ppm of fluoride ion. Among these materials are water-soluble inorganic metal salts, for example, sodium fluoride, potassium fluoride, sodium monofluorophosphate, and sodium fluorosilicate. Sodium fluoride and sodium monofluorophosphate are preferred fluoride-providing salts.

Pyrophosphate salts having anticalculus efficacy useful in the practice of the present invention include water soluble salts such as dialkali or tetra-alkali metal pyrophosphate salts such as $Na_4P_2O_7$ (TSPP), $K_4P_2O_7$, $Na_2K_2P_2O_7$, $Na_2H_2P_2O_7$ and $K_2H_2P_2O_7$. Polyphosphate salts include the water soluble alkali metal tripolyphosphates such as sodium tripolyphosphate and potassium tripolyphosphate.

The pyrophosphate salts are incorporated in the gel or paste composition of the present invention at a concentration of about 0.5 to about 2.0% by weight, and preferably about 1.5 to about 2% by weight and the polyphosphate salts are incorporated in the composition of the present invention at a concentration of about 1.0 to about 3.0% by weight and preferably about 2 to about 3% by weight.

Colorants such as pigments and dyes may be used in the practice of the present invention. Pigments include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C # Yellow 15 lake. The pigments have a particle size in the range of 5–1000 microns, preferably 250–500 microns, and are present at a concentration of 0.5 to 3% by weight.

Dyes used in the practice of the present invention are generally food color additives presently certified under the Food Drug & Cosmetic Act for use in food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-AE-3,5-cyclohexadienimine], FD&C Blue No. 1 (disodium salt of dibenzyldiethyldiaminotriphenylcarbinol trisulfonic acid anhydrite), FD&C Blue No. 2(sodium salt of disulfonic acid of indigotin) and mixtures thereof in various proportions. The concentration of the dye for the most effective result in the present invention is present in the composition in an amount from about 0.0005 percent to about 2 percent of the total weight.

Any suitable flavoring or sweetening material may also be incorporated in the composition of the present invention.

Examples of suitable flavoring constituents are flavoring oils, e.g., oils of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, and sodium saccharin. Suitably, flavor and sweetening agents may together comprise from 0.01% to 5% or more of the preparations.

Various other materials may be incorporated into the composition of this invention. Non-limiting examples thereof include preservatives, silicones and chlorophyll compounds, antibacterial agents such as chlorohexidene, halogenated diphenyl ethers such as Triclosan, desensitizing agents such as potassium nitrate and potassium citrate and mixtures thereof. These adjuvants are incorporated in the gel or paste in amounts which do not substantially adversely affect the properties and characteristics desired.

To prepare the composition of the present invention, the humectants e.g. glycerin and glycol humectants and sweetener are dispersed in a conventional mixer until the mixture becomes a homogeneous gel phase. Into the gel phase are added a colorant, the anticalculus agents and a fluoride anti-caries agent. These ingredients are mixed until a homogeneous phase is obtained. Thereafter the thickener, polishing agent, reactive ingredient such as peroxide, bicarbonate salts, flavor and surfactant ingredients are added and the ingredients mixed at high speed under vacuum of about 20–100 mm Hg. The resultant product is a homogeneous, semi-solid, extrudable paste product.

The following example illustrates the invention further. All proportions and amounts therein and elsewhere in this specification are by weight unless otherwise indicated.

EXAMPLE

To demonstrate the storage stability of the composition of the present invention, a toothpaste composition of the present invention was prepared containing 2% TSPP and 3% STPP and 10% by weight water following the procedure previously described containing the ingredients listed in Table I below. The toothpaste composition was loaded into plastic laminated tubes, sealed and then aged at 120° F. for six weeks. The plastic laminated tube contents were analyzed after the aging period. The analysis results are summarized in Table II below.

TABLE I

TOOTHPASTE COMPOSITION

| Ingredients | Wt. % |
| --- | --- |
| Glycerin | 26.00 |
| Zeodent 115 | 20.00 |
| Propylene Glycol | 12.89 |
| Sodium Bicarbonate | 16.00 |
| Deionized Water | 10.00 |
| Polyethylene Glycol 600 | 3.00 |
| Sodium Tripolyphosphate | 3.00 |
| Hydrated Amorphous Silica | 1.50 |
| NaOH (50% solution) | 1.50 |
| Tetrasodium Pyrophosphate | 2.00 |
| Sodium Lauryl Sulfate | 1.50 |
| Sodium Monofluorophosphate | 0.760 |
| Flavor | 0.95 |
| Sodium Saccharin | 0.500 |
| Titanium Dioxide | 1.00 |
| Calcium Peroxide | 0.500 |
| Carrageenan | 0.200 |

TABLE I-continued

TOOTHPASTE COMPOSITION

| Ingredients | Wt. % |
| --- | --- |
| Sodium Carboxymethyl Cellulose | 0.200 |
| FD&C Green #3 Dye | 0.0014 |
| Total | 100.00 |

TABLE II

Aging of Composition at 120°

| Initial | | 6 Weeks | |
| --- | --- | --- | --- |
| % TSPP | % STPP | % TSPP | % STPP |
| 2.0 | 3.0 | 2.0 | 2.7 |

The results recorded in Table II indicate that the toothpaste composition is substantially storage stable with little or no change in the concentration of TSPP or STPP.

What is claimed is:

1. An aqueous fluoride gel or paste which is storage stable and is effective against calculus, comprising a vehicle containing in excess of about 9% by weight water and up to about 15% by weight water, a water soluble fluoride compound providing about 10 to 2,000 ppm fluoride ion and a combination of about 0.5 to no more than about 3% by weight of a water soluble alkali metal polyphosphate and about 0.5 to no more than about 2.0% by weight of a water soluble alkali metal pyrophosphate which composition is stable and effective to reduce calculus formation on teeth in the oral cavity.

2. The dentifrice composition of claim 1 wherein the water soluble alkali polyphosphate is sodium tripolyphosphate.

3. The dentifrice composition of claim 1 wherein the alkali metal pyrophosphate is sodium pyrophosphate.

4. The dentifrice composition of claim 1 wherein a polyvalent metal compound is incorporated in the vehicle.

5. The dentifrice composition of claim 4 wherein the polyvalent metal compound is a polyvalent metal peroxide.

6. The dentifrice composition of claim 5 wherein the polyvalent metal peroxide is calcium peroxide.

7. The dentifrice composition of claim 1 wherein a bicarbonate compound is incorporated in the vehicle.

8. The dentifrice composition of claim 7 wherein the bicarbonate compound is sodium bicarbonate.

9. The dentifrice composition of claim 1 wherein the fluoride compound is sodium monofluorophosphate.

10. The composition of claim 1 wherein there is incorporated in the vehicle a polyvalent compound, a peroxide compound, a bicarbonate compound and a fluoride compound.

11. A method for reducing calculus of those susceptible of forming calculus and for treating diseases of the oral cavity by applying to the cavity an aqueous fluoride gel or paste which is storage stable and is effective against calculus the dentifrice comprising a vehicle containing in excess of about 9% by weight water and up to about 15% by weight water, a water soluble fluoride compound providing about 10 to 2,000 ppm fluoride ion and a combination of about 0.5 to no more than about 3% by weight of a water soluble alkali metal polyphosphate and about 0.5 to no more than about 2.0% by weight of a water soluble alkali metal pyrophosphate which composition is stable and effective to reduce calculus formation on teeth in the oral cavity.

12. The method of claim 11 wherein the water soluble alkali polyphosphate is sodium tripolyphosphate.

13. The method of claim 11 wherein the alkali metal pyrophosphate is sodium pyrophosphate.

14. The method of claim 11 wherein a polyvalent metal compound is incorporated in the vehicle.

15. The method of claim 14 wherein the polyvalent metal compound is a polyvalent metal peroxide.

16. The method of claim 15 wherein the polyvalent metal peroxide is calcium peroxide.

17. The method of claim 11 wherein a bicarbonate compound is incorporated in the vehicle.

18. The method of claim 17 wherein the bicarbonate compound is sodium bicarbonate.

19. The method of claim 11 wherein the fluoride compound is sodium monofluorophosphate.

20. The method of claim 11 wherein there is incorporated in the vehicle a polyvalent metal compound, a peroxide compound, a bicarbonate compound and a fluoride compound.

* * * * *